(12) United States Patent
Steiner et al.

(10) Patent No.: US 6,783,532 B2
(45) Date of Patent: Aug. 31, 2004

(54) DEVICE FOR REMOVING BONE TISSUE

(75) Inventors: Bèatrice Steiner, Cham (CH); Markus Hehli, Frauenkirch (CH); Max Aebi, Montreal (CA); Thomas Steffen, Montreal (CA)

(73) Assignee: Synthes (USA), Paoli, PA (US)

( * ) Notice: Subject to any disclaimer, the term of this patent is extended or adjusted under 35 U.S.C. 154(b) by 118 days.

(21) Appl. No.: 09/918,459

(22) Filed: Aug. 1, 2001

(65) Prior Publication Data

US 2002/0058945 A1 May 16, 2002

Related U.S. Application Data

(63) Continuation-in-part of application No. PCT/CH00/00046, filed on Jan. 31, 2000, and a continuation-in-part of application No. PCT/CH00/00047, filed on Jan. 31, 2000.

(30) Foreign Application Priority Data

Feb. 2, 1999 (DE) ...................................... 299 01 723 U

(51) Int. Cl.[7] .............................................. A61B 17/16
(52) U.S. Cl. ........................................................ 606/80
(58) Field of Search ............................ 606/79, 80, 170, 606/167, 180, 166

(56) References Cited

U.S. PATENT DOCUMENTS

| 3,528,425 | A | 9/1970 | Banko |
|---|---|---|---|
| 3,584,629 | A | 6/1971 | Hoef et al. |
| 3,732,858 | A | 5/1973 | Banko |
| 3,976,077 | A | 8/1976 | Kerfoot, Jr. |
| 4,445,509 | A | 5/1984 | Auth |
| 4,553,957 | A | 11/1985 | Williams et al. |
| 4,573,979 | A | 3/1986 | Blake |
| 4,646,738 | A | 3/1987 | Trott |
| 4,649,919 | A | 3/1987 | Thimsen et al. |
| 4,735,604 | A | 4/1988 | Watmough et al. |
| 4,751,922 | A | 6/1988 | DiPietropolo |

(List continued on next page.)

FOREIGN PATENT DOCUMENTS

| DE | 197 19 051 A1 | 11/1998 |
|---|---|---|
| EP | 0 440 371 A1 | 8/1991 |
| EP | 0 508 710 A1 | 10/1992 |
| EP | 0 666 059 A2 | 8/1995 |
| EP | 0 836 833 A2 | 4/1998 |
| JP | 5-103790 | 4/1993 |
| JP | 10-118084 | 3/1995 |
| JP | 10-43193 | 2/1998 |
| JP | 10-216138 | 8/1998 |
| WO | WO 96/31307 | 10/1996 |
| WO | WO96/39956 | 12/1996 |
| WO | WO 97/03617 | 2/1997 |
| WO | WO97/16118 | 5/1997 |
| WO | WO97/38635 | 10/1997 |
| WO | WO97/39685 | 10/1997 |

OTHER PUBLICATIONS

K. M. Stürmer, "Measurement of Intramedullary pressure in an animal experiment and propositions to reduce the pressure increase," *Injury 1993*, Supplement 3, pps. S7–S21.

*Primary Examiner*—Eduardo C. Robert
(74) *Attorney, Agent, or Firm*—Pennie & Edmonds LLP

(57) ABSTRACT

A bone tissue removal and harvesting device is disclosed and includes a cutting tool with a cutting head, a longitudinal shaft attached to the cutting head and a drive element. A container is located on the end opposite the cutting head for collection of the removed bone. The shaft can be made flexible to permit torsion and/or bending around the longitudinal axis without damage to the bone. During the cutting operation, the bone tissue is simultaneously removed and suctioned through an opening of the cutting head and conveyed through an axial shaft bore for collection in the container. The container is detachably mounted to the drive element and connected to the shaft so as to avoid substantial pressure drops from the cutting head to the container.

39 Claims, 4 Drawing Sheets

U.S. PATENT DOCUMENTS

| | | | |
|---|---|---|---|
| 4,811,734 A | 3/1989 | McGurk-Burleson et al. | |
| 4,830,000 A | 5/1989 | Shutt | |
| 4,842,578 A | 6/1989 | Johnson et al. | |
| 4,844,064 A | 7/1989 | Thimsen et al. | |
| 4,867,157 A | 9/1989 | McGurk-Burleson et al. | |
| 4,904,238 A | 2/1990 | Williams | |
| 5,007,917 A | 4/1991 | Evans | |
| 5,019,036 A | 5/1991 | Stahl | |
| 5,074,841 A | 12/1991 | Ademovic et al. | |
| 5,112,299 A | 5/1992 | Pascaloff | |
| 5,114,399 A | 5/1992 | Kovalcheck | |
| 5,122,134 A | 6/1992 | Borzone et al. | |
| 5,190,548 A | 3/1993 | Davis | |
| 5,217,479 A | 6/1993 | Shuler | |
| 5,224,929 A | 7/1993 | Remiszewski | |
| 5,269,785 A | 12/1993 | Bonutti | |
| 5,312,408 A | 5/1994 | Brown | |
| 5,322,505 A | 6/1994 | Krause et al. | |
| 5,403,317 A | 4/1995 | Bonutti | |
| 5,405,348 A | 4/1995 | Anspach, Jr. et al. | |
| 5,443,468 A | 8/1995 | Johnson | |
| 5,487,747 A | 1/1996 | Stagmann et al. | |
| 5,489,291 A | 2/1996 | Wiley | |
| 5,556,399 A | 9/1996 | Huebner | |
| 5,569,254 A | 10/1996 | Carlson et al. | |
| 5,569,284 A | 10/1996 | Young et al. | |
| 5,577,517 A | 11/1996 | Bonutti | |
| 5,618,296 A | * 4/1997 | Sorensen et al. | 606/180 |
| 5,685,673 A | 11/1997 | Jarvis | |
| 5,690,634 A | 11/1997 | Muller et al. | |
| 5,693,062 A | 12/1997 | Stegmann et al. | |
| 5,694,951 A | 12/1997 | Bonutti | |
| 5,720,749 A | 2/1998 | Rupp | |
| 5,759,185 A | 6/1998 | Grinberg | |
| 5,792,167 A | 8/1998 | Kablik et al. | |
| 5,913,859 A | 6/1999 | Shapira | |
| 5,913,867 A | 6/1999 | Dion | |
| 5,916,231 A | 6/1999 | Bays | |
| 5,922,003 A | 7/1999 | Anctil et al. | |
| 5,928,241 A | 7/1999 | Menut et al. | |
| 5,935,131 A | 8/1999 | Bonutti | |
| 5,947,972 A | 9/1999 | Gage et al. | |
| 5,951,561 A | 9/1999 | Pepper et al. | |
| 5,968,048 A | 10/1999 | Harder | |
| 5,971,988 A | 10/1999 | Reccius et al. | |
| 5,980,525 A | 11/1999 | Bryant et al. | |
| 6,001,112 A | 12/1999 | Taylor | |
| 6,042,593 A | 3/2000 | Storz et al. | |
| 6,053,923 A | 4/2000 | Veca et al. | |
| 6,132,448 A | 10/2000 | Perez et al. | |

\* cited by examiner

DEVICE FOR REMOVING BONE TISSUE

CROSS-REFERENCE TO RELATED APPLICATION

The present application is a continuation-in-part of the U.S. National Stage designation of International Patent Application PCT/CH00/00046, filed Jan. 31, 2000 and the U.S. National Stage designation of International Patent Application PCT/CH00/00047, also filed Jan. 31, 2000. Both of these applications claims priority to German Application DE/299/01/723.0, filed Feb. 2, 1999. The entire content of each these applications is expressly incorporated herein by reference thereto.

FIELD OF THE INVENTION

The present invention relates to a device for removing bone tissue. More particularly, the invention relates to a device for removing bone tissue in which the cutting tool opens directly into a collection container that is under vacuum pressure. The container includes a filtering unit to collect the removed bone tissue that can be used, for example, as bone grafting material.

BACKGROUND OF THE INVENTION

Implantation of endogenous bone material remains the most efficient method of management in cases of pseudarthrosis, for optimizing the success rate in arthrodesis and when a bone fracture fails to heal. The use of endogenous bone material is more reliable and more effective than the use of synthetic hydroxylapatite materials or exogenous bone grafts, but it necessitates an additional procedure on the patient's body. This can be minimized by limited depth of penetration and by using a cylindrical needle, such as that used to remove bone material for diagnostic purposes. However, this technique is complicated and hazardous because precise control cannot be guaranteed. Therefore, in most cases, the cancellous bone is cut out through a larger skin incision and a large opening at the pelvic brim. Special bone graft collecting instruments permit a secure and reliable method of obtaining endogenous bone grafts through a small incision in the skin, which minimizes unpleasantness and injury to the patient. These devices remove the bone material reliably and can be used with a drill, so that a larger amount of bone can be removed and the possibility of control is better, and furthermore inadvertent puncturing of the cortical portion is minimized. This reliable and effective technique makes it possible to remove endogenous bone grafts for fusions, pseudarthrosis and bone fractures with minimal injury to the donor. Bone grafts are generally removed from the pelvic bone of a patient's body. Usable bone material can also be obtained from the proximal ulna or distal radius.

A method and a device for harvesting tissue is disclosed in U.S. Pat. No. 5,403,317 to Bonutti. This known system comprises a device for percutaneous removal of tissue and consists of a flexible drill shaft and means for driving the shaft. A cutting tip is mounted on the distal end of the shaft for cutting tissue fragments out of the tissue. During the cutting operation, the tissue fragments are pulled through the shaft by a vacuum and collected at a location outside the body. One disadvantage of this known device is that the bone grafts are conveyed through a tube under a reduced pressure, moving them away from the cutting device to a filter or a separation device. The resulting long conveyance pathways for the bone grafts require a strong vacuum on the end of the conveyor line at a distance from the cutting head and offer the possibility of unwanted deposits of bone grafts inside the conveyor line, especially at bends in the line.

International Publication No. WO 97/39685 of Yuan teaches an apparatus for harvesting bone material that has a rigid, transparent shaft in the form of a hollow cylinder wherein the bone chips are collected, the quantity of collected chips being easily visible due to the transparent shaft, a cutting head arranged on the one end portion and means for receiving a turning moment arranged on the other end portion of the shaft. The apparatus is simply screwed into the bone, the cutting head having the function of cutting and removing chips of bone. The bone chips are received and collected in the cavity of the shaft. The collected bone fragments are then, as needed, removed from the shaft by means of a piston which is inserted into the cavity of the shaft from the side opposite the cutting head. As to the source of rotational drive power, the apparatus may be driven by hand or by motor.

Another apparatus of this type for harvesting bone material is known from U.S. Pat. No. 5,556,399 to Huedner. This known apparatus also includes a drilling head with an adjoining, rigid shaft in the form of a hollow cylinder in which the bone chips are collected and from which they are subsequently removed by means of a manually actuated piston which is to be introduced into the cavity from the side of the drilling head.

U.S. Pat. No. 4,646,738 to Trott discloses a device that has an exterior tube-like part and interior tube-like part, whereby at one end of the interior tube-like part a cutting tool is attached. The interior tube-like part is rotatably arranged within the exterior tube-like part, while the exterior tube-like part is manufactured of a deformable material and is selectively bendable. International Publication No. WO 96/39956 of Aust discloses a device that has a thin-walled hollow cylindrical shank which is externally enclosed through a spiral spring.

In general, these prior art devices suffer from the disadvantage that due to the torsional rigidity of the shaft, there is a risk of cutting or penetrating the harder cortical bone during the process of reaming the spongiosa lying between the cortical portion of the bone. Thus, a need exists for an improved device for removing bone tissue.

SUMMARY OF THE INVENTION

The present invention relates to a device for harvesting bone tissue with a cutting tool. The cutting tool can include a rotatable shaft with proximal and distal ends with an axial bore extending therethrough. The cutting tool also has a cutting head rotatably coupled with the shaft and having a through-hole operably associated with the axial bore such that bone removed by the cutting head passes from the through-hole to the bore. If the cutting head is detachable from the shaft, the connection between the cutting head and the shaft can be a screw connection such that it permits a smaller tool set for removal for assembly or disassembly. Other possible types of connections between the cutting head and the shaft include the use of radial pin screws or radial pin connections. The cutting head may also be configured such that it is integral or fixedly connected to the shaft.

The device also includes a drive element for rotating the shaft about the longitudinal axis and a handle for manually operating the device. The device further includes a container, having a central axis, detachably mounted to the drive element and operably associated with the cutting tool such that the central axis of the container is co-linear with the longitudinal axis of the cutting tool. The container is under vacuum such that the vacuum pressure suctions and removes bone from the through-hole to the container through the axial bore. The device is configured so as to permit simultaneous removal and suction of the bone tissue.

The handle is configured such that the drive element, cutting tool and container are freely movable by the handle.

The device can be configured such that the proximal end of the cutting tool opens into the container. The container remains fixed with respect to the longitudinal axis, and there is an airtight connection between the shaft and the container such that the proximal end of the shaft opens into the container and is isolated from the environment.

The container also includes a nozzle for connection of a vacuum line to create the vacuum pressure within the container. Additionally, the container comprises a separation element for separating the bone tissue from the air stream. The separation element can be a screen, filter, baffle, cyclone, or similar devices.

In one embodiment, the container comprises a gasket sealed ball bearing and housing for mounting the container to the shaft of the cutting tool. The gasket can be an O-ring gasket.

The shaft of the cutting tool can include a flexible portion to avoid damage to cortical bone. One embodiment of the flexible shaft is a metal strip wound in a spiral. The shaft can also include a tube composed of either rubber or plastic inserted into the bore of the shaft. Additionally, the wall of the shaft can be constructed like a bellows.

The cutting tool of the device can include a cutting head with a cylinder having proximal and distal ends and a hollow space therethrough. The distal end of the cutting head includes a drill tip with at least one cutting edge and at least one through-hole extending radially from the central longitudinal axis for the purpose of conveying removed bone tissue to the bore of the shaft. The drill tip can be shaped like a sector of a universal ball joint or a calotte sector.

DETAILED DESCRIPTION OF THE PREFERRED EMBODIMENTS

Figure 1:
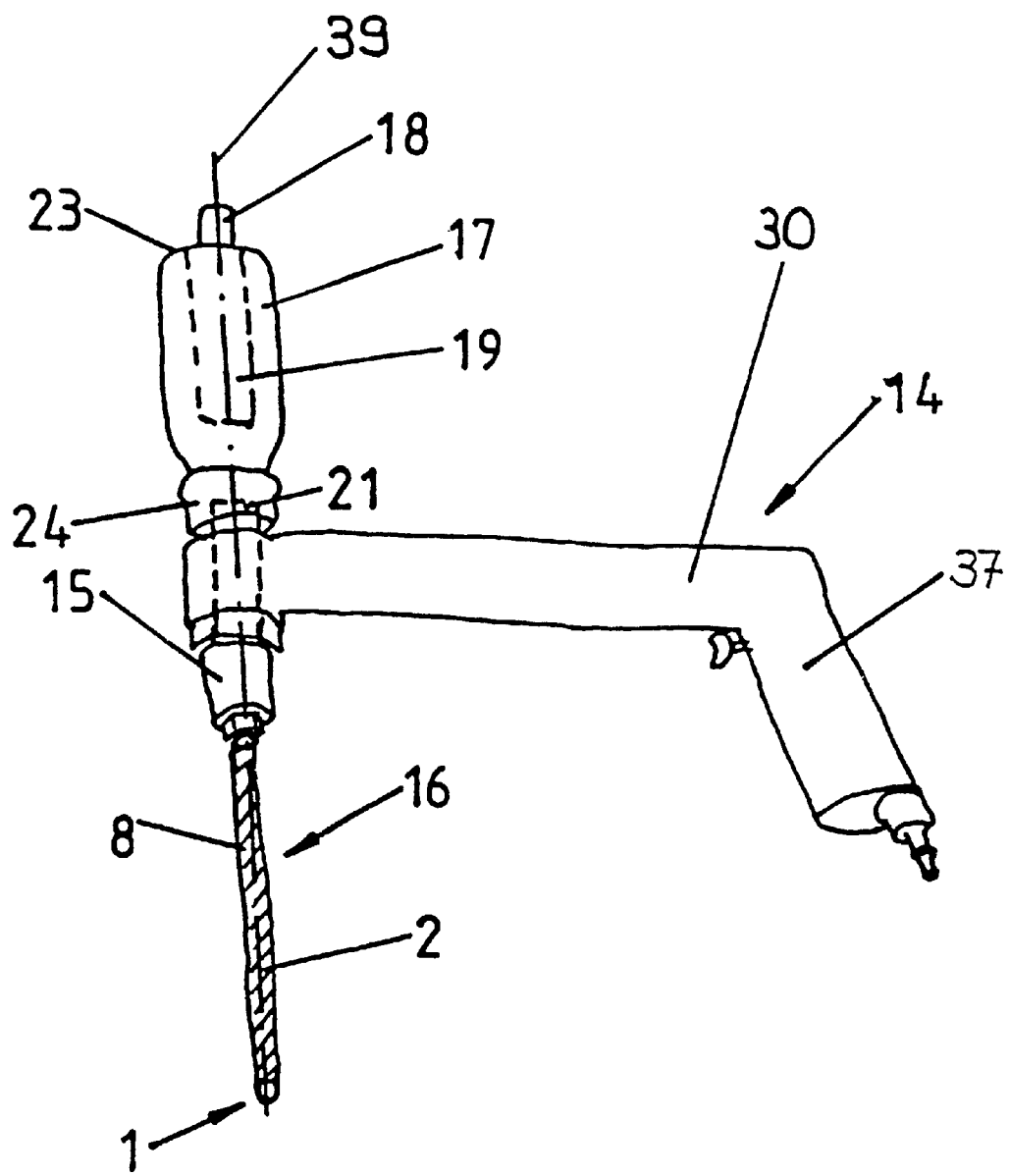
FIG. 1 is a side view of one embodiment of the device according to the present invention.

FIG. 1 shows one embodiment of the device according to the present invention. The cutting tool 16, which is used to harvest the bone grafts, consists of a cutting head 1 with a shaft 8 having proximal and distal ends and including an axial bore 10 running along a longitudinal axis 2. Shaft 8 is secured axially and rotationally in a chuck 15 or other clamping element of a universal drilling machine 30 which serves as the drive element 14. The universal drilling machine 30 is freely movable manually as a complete unit together with the cutting tool 16 and container 17 by means of a handle 37. As discussed below, the arrangement of the components is such that the conveyance pathway for the bone grafts between the site of harvesting (i.e. cutting tool) and the collecting container 17 is as short as possible and the bone grafts are collected in a container connected directly to the drilling tool.

In a bone tissue harvesting operation, drive element 14 imparts a rotational motion upon cutting tool 16 such that cutting head 1, upon contact with bone, drills into the bone to thereby cut and remove the bone tissue. The axial bore 10 of shaft 8 extends from the cutting head 1 at the distal end up to the proximal end 21 of shaft 8, so that the bone grafts can be conveyed along the entire length of the shaft 8. A container 17 for collecting the bone grafts is also mounted on the drive element 14. At its distal end 24, the container 17 is detachably connected to the drive element 14 coaxially with the longitudinal axis 2 so that the proximal end 21 of the shaft 8 is insertably connected to the opening of the container 17 such that it is sealed with respect to the environment. This airtight seal between the shaft 8 of the cutting tool 16 and the container opening, with respect to the environment, can be achieved by mounting the proximal end 21 of shaft 8 without essentially any play in the container opening or by adding a gasket, e.g., an O-ring gasket, on the proximal end 21 of shaft 8 or in the container opening at the distal end 24 of container 17. On its proximal end 23, the container 17 is provided with a nozzle connection 18 to which a vacuum tube (not shown) can be connected. A vacuum pressure is created throughout the interior of the device such that bone tissue removed by cutting head 1 is suctioned and conveyed through shaft 8 to container 17 for collection. The vacuum can operate in a range of pressures. Examples of suitable pressure ranges include from approximately 0 bar to 1 bar, and more particularly in a pressure range of 0.2 bar to 0.8 bar. A separation element 19, such as a screen, is provided in the container 17 so as to prevent bone tissue exiting the nozzle connection 18 and entering the vacuum hose during the harvesting operation. Other types of separation elements 19 that can be used in container 17 include filters, baffles, or cyclones.

Figure 2:
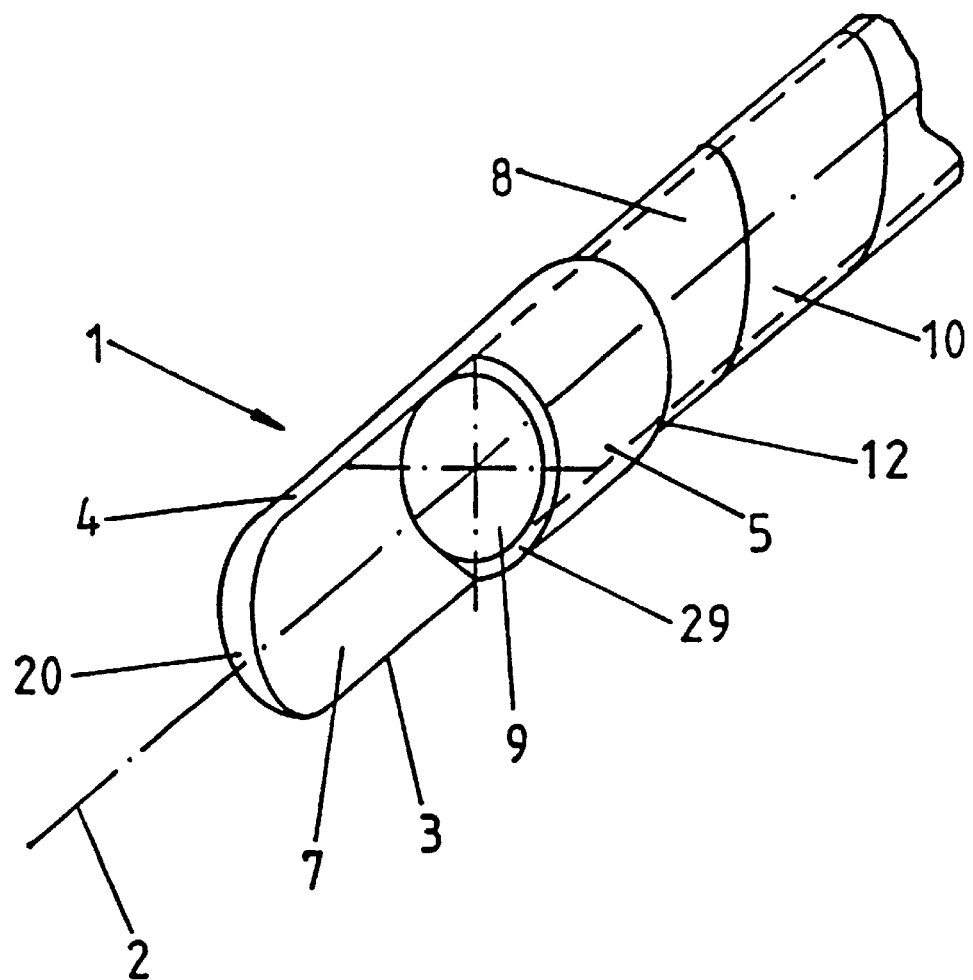
FIG. 2 is a perspective diagram of an embodiment of the cutting head and a portion of the flexible shaft.

FIG. 2 shows an embodiment of the cutting head 1. The cutting head 1 is designed as a hollow cylinder with a longitudinal axis 2 and a drill tip 20 and comprises a distal section 4 connected to the drill tip 20 and a proximal section 5. The distal section 4 consists of a hollow cylinder with a drill tip 20 designed as a calotte sector, i.e. a sector of a universal ball joint, where the side wall of the distal section 4, as seen in cross section at a right angle to the longitudinal axis 2, includes only an annular sector, forming at least one through-hole 7 running radially to the hollow cylindrical part and axially to the drill tip 20. The side wall of the distal section 4 is designed as a cutting edge 3, from the drill tip 20 to the proximal section 5 toward the through-hole 7.

If the rotating cutting head 1 is drilled into the bone, bone grafts are removed by the cutting edges 3 and pass through the through-hole 7 into the hollow space 9 of the cutting head 1, where they are picked up by the vacuum and drawn through the bore 10 in the shaft 8. The present invention also envisions other types of cutting heads that permit simultaneous suction removal and drilling of bone tissue. For example, the hollow cylindrical cutting head 1 may include a drilling tip and cutting edge forming conical sectors with cutting edges and or hollow cylindrical milling cutters with teeth on the end.

Figure 3:
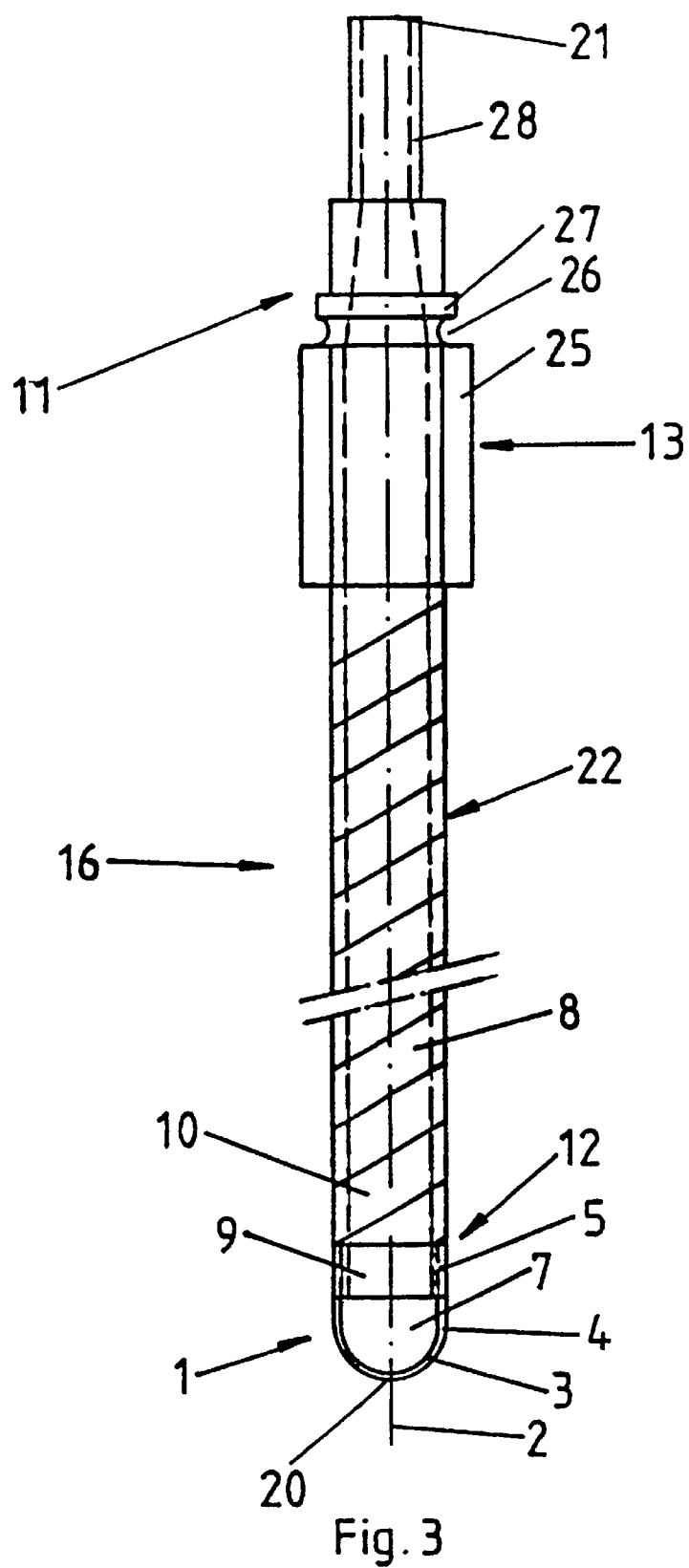
FIG. 3 is a side view of the cutting head and the flexible shaft.

FIG. 3 shows the tool 16 with the cutting head 1 and shaft 8. The shaft 8 comprises a flexible portion 22 which is elastically deformable with respect to torsion and/or bending. Proximal end 21 of shaft 8 includes a means 13 to absorb a torque. Means 13 comprise a section 25 having an hexagonal insert bit 40 and a cylindrical section 27 connected to the former with a groove 26. The two sections 25 and 27 can be connected by a chuck 15 (FIG. 1) on a drive element 14 (FIG. 1), where the shaft 8 is secured detachably in the chuck 15 (FIG. 1) axially by means of the groove 26 and rotationally by means of the hexagonal insert bit 40. The axial bore 10 of shaft 8 extends through the shaft 8 from the cutting head 1 to the proximal end 21 of shaft 8 such that the bone grafts removed by the cutting head 1 can be conveyed along the longitudinal axis 2 through the entire tool 16. To secure the cutting head 1 on the shaft 8, locking screws or spring pins, for example, through shaft 8 and cutting head 1 may be used to secure the cutting head 1 on the shaft 8. Alternatively, the cutting head may be fixedly connected to the shaft.

The flexible portion 22 of the shaft 8 can be made of a metal strip wound in a spiral, with a rubber or plastic tube 36 inserted into the bore 10 (FIG. 4), said tube providing an airtight seal in the bore in tube 36 with respect to the environment. The walls of shaft 8 can be constructed such that they resemble bellows. The elastic deformability of the shaft and a cutting head which is designed without very sharp edges permit removal of the cancellous bone between the cortical portion without thereby cutting or breaking through the harder cortical portion. Toward the proximal end 21 of shaft 8, the shaft is connected to the means 13 for absorbing the torque, so that an airtight seal of this part 28 of shaft 8 with respect to the environment is also possible in the opening into the container 17 (FIG. 1).

Figure 4:
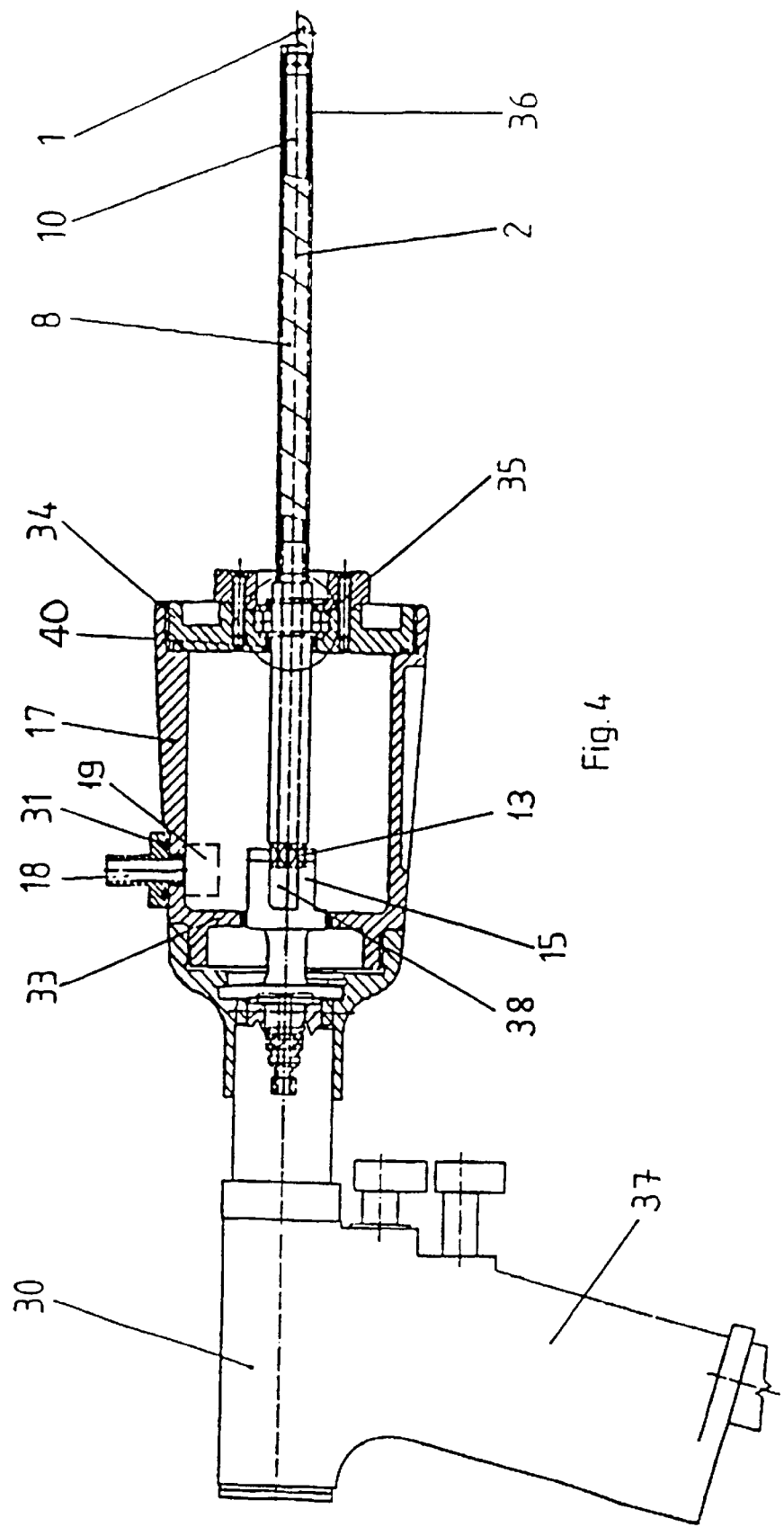
FIG. 4 is a side view of another embodiment of the device according to the present invention.

FIG. 4 shows another embodiment of the device according to the present invention. The embodiment of the device according to the present invention illustrated here differs from the embodiment illustrated in FIG. 1 only in that the cutting tool 16 passes through the container 17 arranged coaxially with the longitudinal axis 2 and the means 13 for absorbing a torque delivered by the universal drilling machine 30 is detachably connected to the universal drilling machine 30 in the area of the container bottom 33. The container 17 with its container bottom 33 is detachably attached to the universal drilling machine 30. Instead of a container cover, a bearing housing 34 is accommodated in the container 17, so that the tool 16 is mounted in said bearing housing with respect to its rotational motion about the longitudinal axis 2 by means of a ball bearing 35, for example. Again in this embodiment, an airtight seal of the cutting tool 16 in the bearing housing 34 with respect to the environment can be achieved by inserting a gasket, e.g., an O-ring gasket 40, between the cutting tool 16 and the bearing housing 34. In addition, the nozzle connection 18 for connecting a vacuum line is mounted on the side wall of the container 17. To seal the flexible shaft 8, a rubber or plastic tube 36 is inserted into its bore 10 along the longitudinal axis 2. The bone grafts removed by the cutting head 1 are conveyed by the vacuum through the bore 10 passing through the tool 16 coaxially with the longitudinal axis 2 up to the proximal end 21 of the tool 16, where they are drawn into the container 17 through openings 38 in the chuck 15. To prevent the bone grafts from being entrained through the connection 18 into the vacuum line (not shown), a separating element 19 which is preferably designed as a screen is mounted in the container 17.

Each of the above disclosed embodiments capture the advantages achieved by this invention which includes its compact design that provides for the cutting tool, the driving element and collection container connected in a single unit that can be freely moved about manually. Additionally the compact design provides for a container arrangement that permits a strong suction power in the device. The flexible shaft design permits reaming of the cancellous bone between the cortical bone in a simple manner without cutting or penetrating the harder cortical portion of the bone.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A bone tissue harvesting device comprising:
   a cutting tool having a longitudinal axis and including a rotatable shaft with proximal and distal ends and an axial bore extending therethrough, and a cutting head coupled to the distal end of the shaft and having a through-hole operably associated with the axial bore such that bone removed by the cutting head passes from the through-hole to the bore;
   a drive element for rotating the shaft about the longitudinal axis and including a handle for manually operating the device; and
   a container, having a central axis, detachably mounted to the drive element and operably associated with the cutting tool such that the central axis of the container is co-linear with the longitudinal axis of the cutting tool, wherein the container is under vacuum such that negative pressure suctions removed bone from the through-hole to the container through the axial bore of the shaft and proximate the proximal end thereof, and wherein the handle is configured and arranged such that the drive element, cutting tool and container are movable by the handle.

2. The device of claim 1 wherein the container further comprises a nozzle connection or connection to a vacuum line.

3. The device of claim 1 wherein the container comprises a separation element for separating the bone tissue from the air stream.

4. The device of claim 3 wherein the separation element is a filter.

5. The device of claim 1 wherein the drive element is a universal drilling machine.

6. A bone tissue harvesting device comprising:
   a cutting tool having a longitudinal axis and including a rotatable shaft with proximal and distal ends and an axial bore extending therethrough, and a cutting head coupled to the shaft and having a through-hole operably associated with the axial bore such that bone removed by the cutting head passes from the through-hole to the bore;
   a drive element for rotating the shaft about the longitudinal axis and including a handle for manually operating the device; and
   a container, having a central axis, detachably mounted to the drive element and operably associated with the cutting tool such that the central axis of the container is co-linear with the longitudinal axis of the cutting tool, wherein the container is under vacuum such that negative pressure suctions removed bone from the through-hole to the container through the axial bore,
   wherein the handle is configured and arranged such that the drive element, cutting tool and container are movable by the handle, and wherein the proximal end of the shaft opens into the container.

7. The device of claim 6, wherein the container remains fixed with respect to the longitudinal axis.

8. The device of claim 7, in the container includes a bearing operably associated with the shaft for mounting on the shaft of the cutting tool.

9. The device of claim 8 wherein the bearing is a gasket sealed bearing.

10. A bone tissue harvesting device comprising:
a cutting tool having a longitudinal axis and including a rotatable shaft with proximal and distal ends and an axial bore extending therethrough, and a cutting head coupled to the shaft and having a through-hole operably associated with the axial bore such that bone removed by the cutting head passes from the through-hole to the bore;
a drive element for rotating the shaft about the longitudinal axis and including a handle for manually operating the device; and
a container, having a central axis, detachably mounted to the drive element and operably associated with the cutting tool such that the central axis of the container is co-linear with the longitudinal axis of the cutting tool, wherein the container is under vacuum such that negative pressure suctions removed bone from the through-hole to the container through the axial bore; and
an airtight seal between the shaft and the container such that the proximal end of the shaft opens into the container and is isolated from the environment;
wherein the handle is configured and arranged such that the drive element, cutting tool and co tamer are movable by the handle.

11. A bone tissue harvesting device comprising:
a cutting tool having a longitudinal axis and including a rotatable shaft with proximal and distal ends and an axial bore extending therethrough, and a cutting head coupled to the shaft and having a through-hole operably associated with the axial bore such that bone removed by the cutting head passes from the through-hole to the bore;
a drive element for rotating the shaft about the longitudinal axis and including a handle for manually operating the device; and
a container, having a central axis, detachably mounted to the drive element and operably associated with the cutting tool such that the central axis of the container is co-linear with the longitudinal axis of the cutting tool, wherein the container is under vacuum such that negative pressure suctions removed bone from the through-hole to the container through the axial bore,
wherein the handle is configured and arranged such that the drive element, cutting tool and container are movable by the handle, and
wherein the shaft includes a flexible portion.

12. The device of claim 11 wherein the flexible portion of the shaft includes a metal strip wound in a spiral.

13. The device of claim 11 wherein a tube is located with the bore of the shaft and the tube is made of rubber or plastic.

14. The device of claim 11 wherein the shaft is made of a metal tube.

15. A bone tissue harvesting device comprising:
a cutting tool having a longitudinal axis and including a rotatable shaft with proximal and distal ends and an axial bore extending therethrough, and a cutting head coupled to the shaft and having a through-hole operably associated with the axial bore such that bone removed by the cutting head passes from the through-hole to the bore;
a drive element for rotating the shaft about the longitudinal axis and including a handle for manually operating the device; and
a container, having a central axis, detachably mounted to the drive element and operably associated with the cutting tool such that the central axis of the container is co-linear with the longitudinal axis of the cutting tool, wherein the container is under vacuum such that negative pressure suctions removed bone from the through-hole to the container through the axial bore, wherein the handle is configured and arranged such that the drive element, cutting tool and container are movable by the handle, and
wherein the cutting head comprises a cylinder having proximal and distal ends with a hollow space therethrough, the distal end having a drill tip with at least one cutting edge and at least one through-hole extending radially from the central longitudinal axis for conveying removed bone tissue to the bore of the shaft.

16. The device of claim 15 wherein the drill tip has a shape like a sector of universal ball joint.

17. A bone tissue harvesting device comprising:
a rotatable shaft comprising a proximal end, a distal end, an axial bore extending from the proximal end to the distal end along a longitudinal axis thereof, and a cutting head disposed proximate the distal end and configured and dimensioned for cutting bone tissue;
a drive element operatively associated with the shaft for rotating the shaft about the longitudinal axis; and
a container disposed along the longitudinal axis for receiving the bone tissue;
wherein the proximal end of the rotatable shaft is disposed within the container.

18. The device of claim 17, wherein the drive element further includes a chuck disposed within the container.

19. The device of claim 18, wherein the shaft further comprises a portion configured and dimensioned to be received by the chuck for positive engagement therewith.

20. The device of claim 17, wherein the shaft further comprises a flexible portion.

21. The device of claim 17, wherein the axial bore communicates with the container at the proximal end of the shaft.

22. The device of claim 17, further comprising a seal between the shaft and the container.

23. The device of claim 17, further comprising a nozzle connection communicating with the container for drawing a vacuum therein.

24. The device of claim 22, further comprising a filter disposed proximate the nozzle connection.

25. The device of claim 17, wherein the shaft further comprises bellows.

26. The device of claim 17, wherein the shaft further comprises a metal portion and a plastic portion.

27. The device of claim 17, wherein the cutting head is detachably mounted to the shaft.

28. The device of claim 17, wherein the cutting head is fixedly connected to the shaft.

29. The device of claim 17, wherein the cutting head is disposed about the outer surface of the shaft.

30. The device of claim 17, wherein the cutting head comprises cutting edges forming conical sectors.

31. The device of claim 17, wherein the cutting head is configured and dimensioned for cutting cancellous bone tissue.

32. A bone tissue harvesting device comprising:
- a rotatable shaft comprising a proximal end, a distal end, an axial bore extending from the proximal end to the distal end along a longitudinal axis thereof, and a cutting head disposed proximate the distal end and configured and dimensioned for cutting bone tissue;
- a drive element operatively associated with the shaft for rotating the shaft about the longitudinal axis; and
- a container disposed along the longitudinal axis for receiving the bone tissue;
- wherein the proximal end of the rotatable shaft is disposed proximate an end of the container.

33. The device of claim 32, wherein the drive element further includes a chuck.

34. The device of claim 33, wherein the chuck is disposed within the container.

35. The device of claim 33, further comprising a handle disposed transverse to the longitudinal axis intermediate the chuck and the container.

36. The device of claim 33, further comprising a handle offset from the longitudinal axis intermediate the chuck and the container.

37. The device of claim 32, further comprising a nozzle connection communicating with the container for drawing a vacuum therein and a filter disposed proximate the nozzle connection.

38. The device of claim 37, wherein the nozzle connection is disposed proximate the longitudinal axis.

39. The device of claim 37, wherein the cutting head is configured and dimensioned for cutting cancellous bone tissue.

* * * * *

UNITED STATES PATENT AND TRADEMARK OFFICE
CERTIFICATE OF CORRECTION

PATENT NO. : 6,783,532 B2
DATED : August 31, 2004
INVENTOR(S) : Steiner et al.

It is certified that error appears in the above-identified patent and that said Letters Patent is hereby corrected as shown below:

Column 6,
Line 39, please replace "or" with -- for --;

Column 7,
Line 5, please replace "in" with -- wherein --;
Line 32, please replace "co tamer" with -- container --.

Signed and Sealed this

Ninth Day of November, 2004

JON W. DUDAS
*Director of the United States Patent and Trademark Office*